United States Patent [19]

Sherif

[11] Patent Number: 5,034,550

[45] Date of Patent: Jul. 23, 1991

[54] PROCESS FOR FORMING MIXED HEAVY BIMETAL ALKOXIDE-CARBOXYLATE COMPOSITIONS AND NOVEL COMPOSITIONS THEREOF

[75] Inventor: Fawzy G. Sherif, Stony Point, N.Y.

[73] Assignee: Akzo nv, Arnhem, Netherlands

[21] Appl. No.: 534,824

[22] Filed: Jun. 7, 1990

Related U.S. Application Data

[63] Continuation-in-part of Ser. No. 469,642, Jan. 24, 1990, abandoned.

[51] Int. Cl.$^5$ .............................. C07F 7/00; C07F 5/00
[52] U.S. Cl. ........................................ 556/54; 556/51; 534/16
[58] Field of Search ................. 556/51, 52, 54; 534/16

[56] References Cited

U.S. PATENT DOCUMENTS 4,609,755 9/1986 Farrar ............................... 556/54 X
4,681,959 7/1987 Ayen et al. ............................ 556/54

*Primary Examiner*—Arthur C. Prescott
*Attorney, Agent, or Firm*—Richard P. Fennelly; Louis A. Morris

[57] ABSTRACT

Mixed heavy bimetallic alkoxide-carboxylate compositions are formed by reaction of a heavy metal tetraalkoxide (e.g., a zirconium alkoxide) and a heavy metal tricarboxylate (e.g., yttrium acetate) with elimination of distillable ester by-product therefrom. Hydrolysis of said compositions produced novel bimetallic hydroxycarboxylates. Calcination of the hydrolysis products give bimetallic oxides.

17 Claims, No Drawings

PROCESS FOR FORMING MIXED HEAVY BIMETAL ALKOXIDE-CARBOXYLATE COMPOSITIONS AND NOVEL COMPOSITIONS THEREOF

This is a continuation-in-part of U.S. Ser. No. 469,642, filed Jan. 24, 1990 now abandoned.

BACKGROUND OF THE INVENTION

It is known from U.S. Pat. No. 4,507,245 to react a rare earth metal alkoxide and an alkali metal alkoxide in an inert organic solvent under anhydrous conditions to yield a rare earth alkoxide of the formula $(MOR)_3$ where M is a rare earth metal and R is an alkyl group. Such alkoxides contain a single metal atom.

Certain disclosures also exist in the art in regard to producing products containing a heavy metal atom, alkoxide moieties and the trimethylsilyl moiety ($R_3SiO$). Such products are formed by reacting a heavy metal alkoxide with the covalent compound trimethylacetoxysilane and are disclosed in D. C. Bradley, J. Chem. Soc., 3404–3411 (1957); P. P. Sharma et al., Indian J. Chem., Vol. 5, September 1967, 456–457; R. C. Mehrotra et al., J. Indian Chem. Soc., Vol. 44, No. 3, 1967, pp. 223–224; R. C. Mehrotra et al., J. Indian Chem. Soc., Vol. 44, No. 4, 1967, pp. 345–346; and J. M. Batwara et al., J. Inorg. Nucl. Chem., 1970, Vol. 32, pp. 411–415.

Aluminum sec-butoxide was reacted with acetic acid as described by A. Ayral et al., J. Mater. Res., Vol. 4, No. 4, 1989, pp. 967–971. Sec-butyl alcohol was detected as a product initially, followed by sec-butyl acetate ester. This led the authors to propose an intermediate structure containing aluminum monobutoxide-diacetate which formed a basic acetate upon hydrolysis. The authors did not separate or identify the intermediate they produced.

Other condensation products have been reported (i.e., in U.S. Pat. No. 2,621,193) where titanium alkoxides are reacted with organic acids to get mixed alkoxide-carboxylate compositions of a single metal, for example, titanium.

U.S. Pat. No. 4,122,107 to J. F. Kenney discloses catalysts which are the reaction products of specific antimony or zirconium (IV) compounds with a carboxylate of calcium, manganese or zinc and an acid anhydride, alcohol, or glycol. Col. 3, lines 46–47 indicate that the product is a bimetallic alkoxide "or" carboxylate. Bimetallic alkoxide-carboxylate compositions are not disclosed.

M. Osgan et al. in Polymer Letters, Vol. 88, pp. 319–321 (1970) describe previous work reported in U.S. Pat. No. 3,432,445 dealing with condensation products of certain bivalent metal compounds (e.g., zinc acetate) as catalysts and trivalent metal compounds (e.g., aluminum alcoholates) and indicate that the proposed species (i.e., mu-oxo-alkoxides of aluminum and zinc) were not formed but that the condensation products contained some residual acetato groupings and some higher condensed species. Osgan et al. therefore proposed to form the desired condensation products by "some other independent way", namely, by the controlled hydrolysis of aluminum and zinc alkoxides under alcoholysis conditions.

SUMMARY OF THE INVENTION

The instant invention relates to a novel process for forming novel mixed heavy bimetal alkoxide-carboxylate compositions by reacting a heavy metal tetraalkoxide and a different heavy metal tricarboxylate with elimination of distillable ester by-product therefrom.

DETAILED DESCRIPTION OF THE INVENTION

The invention described below demonstrates that by reacting one or more metal alkoxides with one or more trivalent metal carboxylates (e.g., acetates), rather than with the free acid, condensation of multimetal moieties occurs with the liberation of an alkoxy-carboxylate from the reaction mixture. The invention demonstrates that condensed metal-metal alkoxide-carboxylate compositions are formed. This molecularly uniform species contains two or more metals and is useful as a raw material for making uniform films and uniform electronic precursors for advanced ceramics. Upon hydrolysis, uniform bimetallic compositions useful for structural ceramics and powders for plasma spray coatings, for example, can be formed.

The heavy metal tetraalkoxide reactant intended for use in regard to the instant invention, in one embodiment thereof, is of the formula

where M is a tetravalent heavy metal of the transition metal series and includes zirconium, titanium, and hafnium. The group R is alkyl, either straight chain or branched, having from about 1 to about 5 carbon atoms.

The heavy metal tricarboxylate intended for reaction with the previously described tetraalkoxide is of the formula

where $M^1$ is a trivalent heavy metal of the transition metal series such as aluminum, iron, and chromium and includes the rare earth metals (scandium, yttrium and the lanthanides). The group $R^1$ is a lower alkyl of from about 1 to about 4 carbon atoms, preferably methyl.

The tricarboxylate is reacted in its anhydrous form in accordance with the present invention. Hydrated compounds need to be carefully dehydrated so as to avoid decomposition of one or more of the carboxylate groups by over drying. Such over drying will result in a basic salt which is difficult to solubilize and react with the metal alkoxide. Under heating, on the other hand, may not remove all of the water of hydration. Such water will prehydrolyze the metal alkoxide thereby forming localized gels which render the reaction mixture non-uniform.

The aforementioned tetraalkoxide and tricarboxylate can be reacted together under anhydrous conditions (e.g., in a substantially anhydrous organic solvent) at molar ratios of about 1:10 to about 10:1 at temperatures of from about 20° C. to about 120° C. with elimination of distillable ester by-product (e.g., acetate by-product) therefrom. The reaction which results in the elimination of the ester by-product is not a reversible reaction so there is no need to remove the by-product by distillation. However, if desired, a distillation step to remove the ester by-product can be used.

The reaction in accordance with the present invention can also be carried out between a tetravalent heavy metal carboxylate (e.g. acetate) and a heavy metal trialkoxide. In the former case the metal can be a transition metal such as zirconium, titanium, and hafnium. In the latter, such transition metals as aluminum, iron, chromium, scandium, yttrium, and the lanthanides can be chosen.

The reaction in accordance with either embodiment described above can advantageously be initially carried out so that the trivalent and tetravalent metal precursors thereof give a final composition (after hydrolysis) containing a maximum of about 90%-96% by weight of $MO_2$ and at least 4%-10% by weight of $M^1_2O_3$. The latter oxide stabilizes the crystalline phase of the former. Exemplary compositions are yttria-stabilized zirconia, ceria-stabilized zirconia, and the like. Such stabilized oxides are suitable as thermally resistant material for coatings. A preferred coating contains 8% yttria and 92% zirconia and is a suitable powder containing non-transformable tetragonal zirconia recommended for plasma spray coating applications.

This invention also demonstrated that by reacting the metal alkoxide with a trivalent metal acetate in a molar ratio of 1:1 or 2:1, respectively, condensation of the two metal species occurred. In addition, the loss of one alkoxide group with one carboxylate (e.g., acetate) group formed one mole of an alkoxy-carboxylate ester which was eliminated from the reaction mixture. Determination of the quantity of this eliminated ester allowed for balancing of the reaction. Furthermore, one extra alkoxide group in a 1:1 ratio or two extra alkoxide groups in a 2:1 ratio decomposed to olefins. Thus, a novel compound of the 1:1 reactants, where the ratio of alkoxide to carboxylate is 1:1, was left behind:

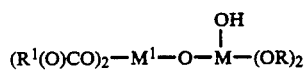

where M, R, $M^1$ and $R^1$ are as previously described. A novel compound can be also derived from the 2:1 reactants:

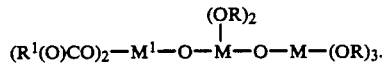

where the ratio of alkoxide to carboxylate is 5:2. While chemical analysis of the products indicates that the above structures are generally valid, the exact structures are not precisely known in every detail. The compositions achieved appear to depend upon the ratio of the alkoxide to carboxylate. It is probable that the reaction product contains the above compositions (as appropriate) in addition to higher condensed forms of such compositions.

The 1:1 reaction can be represented by the following reaction in the case of reaction of zirconium butoxide and yttrium acetate:

$Y(OCOCH_3)_3 + Zr—(OC_4H_9)_4 \longrightarrow$

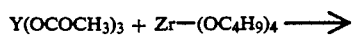

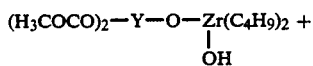

The 2:1 reaction, using the same reactants, can be represented as follows:

$Y(OCOCH_3)_3 + 2Zr—(OC_4H_9)_4 \longrightarrow$

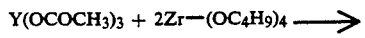

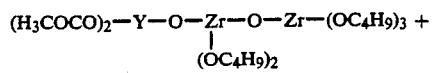

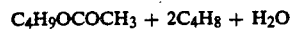

The raw material used for the tetravalent alkoxide can be an alkoxide.alcohol complex such as $M(OR)_4\cdot ROH$ which is a commercially available product. In this case, in addition to the separated ester as described above, one mole of alcohol for every mole of metal alkoxide can be distilled therefrom. The ester-alcohol usually forms an isotrope and can be distilled off at a slightly lower temperature than when using the alkoxide without the alcohol.

The compound formed and described above in connection with the 1:1 reaction can be further hydrolyzed, as shown in Example 10 to yield an acetate/hydroxide, for example, of the formula $(CH_3COO)_2$—Y—O—Zr—$(OH)_3$. Analogously, the mixed metal compound formed from the 2:1 reaction can also be further hydrolyzed as shown in Example 11 to form the acetate/hydroxy compound of the formula

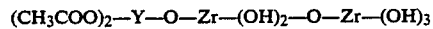

If desired, this can be extrapolated to other metal moieties M and $M^1$ as those terms are earlier described.

Upon firing of the above compositions a mixed metal oxide is formed, with liberation of water, alcohol and organic combustion by-products, to yield a substantially chemically uniform oxide having the following repeat unit:

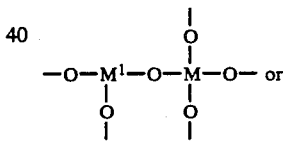

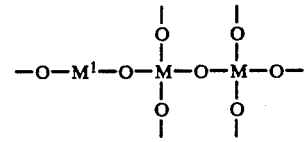

where the ratio of $M^1$ to M can range from about 1:10 to about 10:1.

The present invention is further illustrated by the Examples which follow.

EXAMPLE 1

This Example illustrates the preparation of a mixed metal alkoxide carboxylate of yttrium and zirconium.

Anhydrous yttrium acetate (69.4 gm) was mixed with 1218 gm of a zirconium butoxide-butanol complex (commercially available from Alfa Products, Morton Thiokol, Inc.) in a five liter round bottom flask. The mixture was heated to reflux and held until all the yttrium salt was solubilized. Volatiles were distilled off at 112°–123° C. The distillate weighed 232.3 gm and comprised 176.5 gm of butanol and 55.8 gm of butyl acetate indicating reaction of the yttrium salt with the zirconium compound. The viscous liquid product residue (1004.2 gm) was soluble in heptane.

The solubilized product can be used as a chemically uniform raw material for forming yttria-stabilized zirconia by plasma spray coating procedures.

EXAMPLE 2

This Example illustrates the preparation of 8% yttrium oxide by emulsion hydrolysis of the salt and alkoxide.

Anhydrous yttrium acetate (69.6 gm) was mixed with 1225 gm of zirconium n-propoxide solution containing 73.6% zirconium isopropoxide in propanol in a five liter round bottom flask under nitrogen atmosphere. The mixture was heated to reflux and held until the yttrium salt went into solution.

The remaining solution was cooled down to room temperature, 2200 gm of n-heptane was added, and the resulting solution was stirred vigorously. Water (213 cc) was then added and the stirring of the resulting emulsion was continued until gelation occurred. The gel was stored for four hours and then broken with more stirring for thirty minutes.

The powdery gel that resulted was filtered from the solution using a Buchner funnel and was washed with 500 cc of n-heptane. The filter cake was dried at 125° C. for four hours and then was milled gently until all the powder passed through a 140 mesh screen. The powder was calcined at 200°, 400°, 800°, and 1100° C. each for two hours. The weight of calcined powder was 354 gm. The powder was classified by sieving through a 500 mesh screen using an Alpine air jet sieve. The yield was 260 gm.

The properties of the classified powder were as follows:

| Median Particle Size: | 57 microns |
| Bulk Density | 2.1 gm/cc |
| Flow Rate: | 1.7 cc/sec |
| Crystalline Phase: | Nontransformable Tetragonal Zirconia |

The powder was judged acceptable for use in plasma spray coatings. This is indicated by the following properties:

| Deposition Efficiency | 54% |
| Feed Rate | 38 gm/min |
| Cross-sectional Coat Porosity | 15-20% |
| Rockwell Hardness of Coating | 85 |
| Adhesion | 3116 lbs/in$^2$ |

EXAMPLE 3

This Example illustrates the preparation of 8% yttrium oxide by emulsion hydrolysis of the salt and alkoxide.

Anhydrous yttrium acetate (69.6 gm) was mixed with 1215 gm of zirconium n-butoxide butanol complex (from Alfa Products, Morton Thiokol, Inc.) in a five liter round bottom flask under nitrogen atmosphere. The mixture was heated to reflux and held until the yttrium salt went into solution. A liquid (250 gm) was then distilled from the solution. It contained the butanol/butyl acetate isotrope (22.8 wt % butyl acetate).

The remaining solution was cooled down to room temperature, 2200 gm of toluene was added, and the resulting solution was stirred vigorously. Water (213 cc) was then added and the stirring of the resulting emulsion was continued until gelation occurred. The gel was stored for four hours and then broken with more stirring for thirty minutes.

The powdery gel that resulted was filtered from the solution using a Buchner funnel and was washed with 500 cc of toluene. The filter cake was dried at 125° C. for four hours and then was milled gently until all the powder passed through a 140 mesh screen. The powder was calcined at 200°, 400°, 800°, and 1100° C. each for two hours. The weight of powder was 356.8 gm. The powder was classified by sieving through a 500 mesh screen using an Alpine air jet sieve. The yield was 260 gm.

The properties of the classified powder were as follows:

| Median Particle Size: | 76 microns |
| Bulk Density | 1.4 gm/cc |
| Flow Rate (ASTM B 213-48 [1970]): | 0.8 cc/sec |
| Crystalline Phase: | Nontransformable Tetragonal Zirconia |
| Grain Size: | 0.05-0.2 micron |
| Grain Morphology: | Spherical |

The powder was judged acceptable for use in plasma spray coatings.

EXAMPLE 4

This Example was the same as Example 2 except that the non-polar solvent used was cyclohexane. The weight of the 1100° C. calcined metal oxide was 344.2 gm. The weight of the classified powder was 276.0 gm and had the following properties:

| Median Particle Size: | 53 microns |
| Bulk Density | 1.67 gm/cc |
| Flow Rate: | 1.15 cc/sec |

The powder had a high density and good flow and was judged suitable for plasma spray coating applications.

EXAMPLE 5

Forty grams (0.15 mole) of anhydrous yttrium acetate, from Alfa Products, were mixed with 65 cc (0.15 mole) of zirconium n-butoxide-butanol complex, also from Alfa Products, in a five hundred milliliter round bottom flask. The mixture was heated to 130° C. and the yttrium acetate went into solution. Vapors were distilled off and were collected at 112°-114° C. The temperature of the reaction mixture slowly increased to 170° C., and heating was stopped.

The product from the foregoing procedures was a waxy material having a weight of 69 gm. Analysis of the uncondensed gaseous product showed the presence of butene. The condensed distillate (29.6 gm) was colorless and, when analyzed by gas chromatography, was found to contain 0.15 mole butyl acetate and 0.30 mole free butanol. The total butyl group content of 0.45 mole demonstrated that the yttrium and zirconium compounds reacted to form a condensation product.

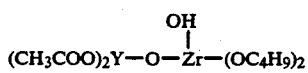

Analysis of the product showed: C=30.92%; H=5.12%; Zr=18.93%; and Y=19.80%. Calculated values for the above product with a molar ratio of Zr:Y of 1:1 were: C=30.69%; H=5.33%; Zr=19.45%; and Y=18.95%.

NMR results showed that the ratio of acetate to alkoxy groups in the composition approached 1:1. The infrared spectra of the composition showed bands at 1575 cm$^{-1}$ corresponding to acetate ion and at 1150 and 1050 cm$^{-1}$ corresponding to the alcoholic C—O stretching vibration of the primary saturated butoxide.

The condensation product dissolved in toluene, butanol, n-heptane, methanol, and ether. It can be applied to form coatings on substrates, such as alumina, by dip coating or spray coating. It can also be used as a raw material for producing uniform ceramic powders for plasma spray coating techniques.

EXAMPLE 6

This Example is similar to Example 5 except that the zirconium tetrabutoxide.butanol complex was predistilled to remove free butanol. The amount of alcohol distilled off from the zirconium butoxide.butanol complex was 23.1 gm (0.31 mole). Eighty grams (0.30 mole) of anhydrous yttrium acetate was added to the resulting (115.3 gm, 0.3 mole) zirconium butoxide. The mixture was heated to 130° C., and the solid yttrium acetate went into solution. The temperature was raised slowly to 195° C. and the distillate (37.6 gm, 0.3 mole) which was collected was butyl acetate. This indicated that the yttrium and zirconium compounds had condensed into a single entity containing a 1:1 molar ratio of Zr to Y.

EXAMPLE 7

Forty grams of anhydrous yttrium acetate (0.15 mole) was mixed with 130 cc of zirconium n-butoxide-butanol complex (0.30 mole) in a 500 ml round bottom flask. The mixture was heated to 130° C. and the yttrium acetate went into solution. Vapors were distilled off at 112°-114° C. and were collected in a receiver. The temperature of the reaction mixture slowly increased to 180° C. Heating was then discontinued.

The product was a waxy material, soluble in toluene and butanol. Its weight was 117.5 gm. Analysis of the uncondensed gaseous product showed the presence of butene. The condensed distillate was colorless (53 gm) and, when analyzed by gas chromatography, was found to contain 0.15 mole butyl acetate and 0.3 mole butanol. The total butyl group content of 0.45 mole showed that the yttrium and zirconium compounds reacted to form a condensation product. Analysis of this product showed a molar ratio of Y to Zr of 1:2: C=36.88%; H=6.39%; Zr=23.15%; and Y=11.95%. The calculated values for a product of the formula

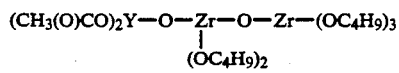

were: C=36.63%; H=6.49%; Zr=23.20%; and Y=11.31%. NMR analysis showed that the ratio of acetate to alkoxy groups approached 2:5. The infrared spectra of the composition showed bands at 1575 cm$^{-1}$ corresponding to acetate ion and at 1150 and 1050 cm$^{-1}$ corresponding to the alcoholic C—O stretching vibration of the primary saturated butoxide.

The product dissolved in toluene, butanol, n-heptane, methanol and ethyl ether. It can be used to form coatings.

EXAMPLE 8

This Example is similar to Example 7 except that the zirconium tetra-butoxide complex was predistilled to remove the free butanol. Two hundred sixty grams of the complex (0.60 mole) was distilled and 41.7 gm of butanol (0.56 mole) was collected. The residue was mixed with 80 gm of anhydrous yttrium acetate (0.3 mole) and the mixture was treated as in Example 7. The butyl acetate distilled from the reaction was 34.2 gm (0.29 mole). This indicated that the Y and Zr compounds condensed into a single entity containing a 1:2 molar ratio of Y to Zr.

EXAMPLE 9

This Example illustrates how yttrium triacetate tetrahydrate was dehydrated to the anhydrous salt which dissolved completely in the reaction mixture of zirconium alkoxide of the previous Examples.

The hydrated triacetate, 248.1 gm, was heated at 120° C. for twenty-four hours. The weight of the material after heating was 193.9 gm. The weight loss was 21.85% as compared to the theoretical weight loss due to four moles of water per mole of the hydrated triacetate of 21.57%.

If the dehydration were not substantially complete, the residual water would prereact with the zirconium alkoxide forming insoluble localized gels, and the mixture would not be substantially uniform prior to its hydrolysis. If the dehydration is carried too far, part of the acetate would be lost and the resultant basic acetate would not dissolve in the reaction mixture. This demonstrates that the dehydration process is of major importance to the instant process.

EXAMPLE 10

The compound $(CH_3COO)_2$—Y—O—Zr—(OH)-$(OC_4H_9)_2$, 19.9 gm (0.04 mole), was dissolved in 30 cc toluene. Water (6.1 cc) was then added, and the mixture was shaken vigorously and was left to settle for sixteen hours. It was then filtered. The white powder that was produced in solution was air dried. Gas chromatography analysis of the filtrate showed it to contain 0.07 mole of free butanol indicating that hydrolysis of the alkoxide took place, but not of the acetate. Infrared analysis of the powder showed a wide band at 3400 cm$^{-1}$ assigned to the presence of OH groups and a sharp band at 1550 cm$^{-1}$ corresponding to the presence of ionic acetate ion. The chemical analysis agreed with the formula $(CH_3COO)_2$—Y—O—Zr—$(OH)_3$:

Found: % C:12.42, H:2.79, Zr:25.10, Y:23.6; Calcd.: % C:13.15, H:2.47, Zr:24.98, Y:24.35

The loss on ignition of the above composition was found to be 32% at 800° C.; calculated for the removal of all organic and water gave 32%. Differential scanning calorimetry in air showed one combustion peak at 363° C. corresponding to the acetate.

EXAMPLE 11

This Example is similar to Example 10 with the exception that the starting material was a compound containing one yttrium atom and two zirconium atoms. The reaction which occurred is represented by the following equation:

$$(CH_3COO)_2-Y-O-Zr-(OC_4H_9)_2-O-Zr-(OC_4H_9)_3 + H_2O$$
$$\rightarrow (CH_3COO)_2-Y-O-Zr-(OH)_2-O-Zr-(OH)_3 \cdot H_2O$$

The product formed, a hydroxy acetate containing multimetal moieties, in the above equation was a solid which was filtered and washed with heptane and dried at 125° C. for six hours. Elemental analysis of the powder gave: C=7.56%; H=1.85%; Y=16.8%; and Zr=35.7%. Calculated values: C=9.16%; H=2.48%; Y=16.96%; and Zr=34.79%.

The loss on ignition of the above composition was found to be 32% at 800° C.; calculated for removal of all volatile 31.5%. Differential scanning calorimetry in air showed one combustion peak at 363° C. corresponding to the acetate.

I claim:

1. A process for forming a mixed heavy bimetallic alkoxide-carboxylate composition which comprises reacting a heavy metal tetraalkoxide and a different heavy metal tricarboxylate under substantially anhydrous conditions with elimination of distillable ester by-product therefrom.

2. A process as claimed in claim 1 wherein at least one heavy metal is a transition metal.

3. A process as claimed in claim 2 wherein the transition metal is selected from the group consisting of yttrium and zirconium.

4. A process as claimed in claim 1 wherein the process is conducted in an organic solvent.

5. A process as claimed in claim 1 wherein the carboxylate is an acetate.

6. A process as claimed in claim 5 wherein at least one heavy metal is a transition metal.

7. A process as claimed in claim 6 wherein yttrium and zirconium are present as heavy metals.

8. A process as claimed in claim 1 where the process is conducted in the substantial absence of solvent.

9. A process as claimed in claim 1 where the process is conducted in a non-polar solvent.

10. A process as claimed in claim 7 wherein the yttrium to zirconium molar ratio varies from about 1:10 to about 10:1.

11. A process as claimed in claim 1 wherein the mixed heavy metal alkoxide carboxylate composition is hydrolyzed with water in a non-aqueous solvent to yield a powder suitable for ceramic plasma spray coatings.

12. A novel composition comprising a bimetallic alkoxide-carboxylate composition of the formula $$(R^1(O)CO)_2M^1-O-M(OH)(OR)_2$$

where $M^1$ is a trivalent heavy metal, M is a tetravalent heavy metal, and R is alkyl and $R^1$ is lower alkyl.

13. A novel mixed heavy metal alkoxide carboxylate having the formula $$(R^1(O)CO)_2-M^1-O-M\overset{\displaystyle (OR)_2}{\underset{\displaystyle |}{}}-O-M-(OR)_3$$

where M is a tetravalent heavy metal, $M^1$ is a trivalent heavy metal, R is alkyl and $R^1$ is lower alkyl.

14. A novel mixed heavy metal carboxylate hydroxide having the formula $$(R^1(O)CO)_2-M^1-O-M(OH)_3$$

where M is a tetravalent heavy metal, $M^1$ is a trivalent heavy metal, and $R^1$ is lower alkyl.

15. A novel mixed heavy metal carboxylate hydroxide having the formula $$(R^1(O)CO)_2-M^1-O-M(OH)_2-O-M(OH)_3 \cdot H_2O$$

where M is a tetravalent heavy metal, $M^1$ is a trivalent heavy metal, and $R^1$ is lower alkyl.

16. A mixed heavy metal oxide condensation product having a repeat unit selected from the group consisting of:

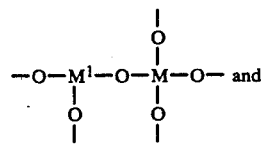 and

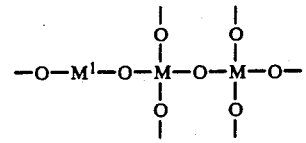

where M is a tetravalent heavy metal and $M^1$ is a trivalent heavy metal.

17. A condensation product as claimed in claim 16 wherein the ratio of $M^1$ can range from about 1:10 to about 10:1.

* * * * *